United States Patent
Harrison et al.

[11] 3,982,422
[45] Sept. 28, 1976

[54] MEANS FOR MEASURING THE WAX CONTENT OF WAXY OIL

[75] Inventors: Charles W. Harrison, Nederland; Theodore C. Mead, Port Arthur; Howard R. Moreland, Houston; Frank L. Barger, Port Arthur, all of Tex.

[73] Assignee: Texaco Inc., New York, N.Y.

[22] Filed: May 8, 1975

[21] Appl. No.: 575,760

[52] U.S. Cl. .................................. 73/53; 73/61 R; 235/151.35
[51] Int. Cl.² ......................................... G01N 11/00
[58] Field of Search ................. 73/61 R, 61.1 R, 53, 73/32 R; 23/230 R, 230 HC; 235/151.35

[56] References Cited
UNITED STATES PATENTS

| | | | |
|---|---|---|---|
| 3,546,109 | 12/1970 | Woodle | 73/32 R X |
| 3,557,609 | 1/1971 | Woodle | 73/53 |
| 3,720,096 | 3/1973 | Woodle | 73/53 |

Primary Examiner—Richard C. Queisser
Assistant Examiner—Joseph W. Roskos
Attorney, Agent, or Firm—Thomas H. Whaley; Carl G. Ries; Ronald G. Gillespie

[57] ABSTRACT

The 50% boiling point, the gravity and the viscosity of waxy oil are sensed by sensors which provide corresponding signals. A computing circuit connected to the sensors provides a signal corresponding to the wax content of the waxy oil in accordance with the signals from the sensors and equations hereinafter disclosed.

18 Claims, 2 Drawing Figures

MEANS FOR MEASURING THE WAX CONTENT OF WAXY OIL

BACKGROUND OF THE INVENTION

1. Field of the Invention

The apparatus of the present invention relates to measuring apparatus in general, and more particularly, to measuring apparatus for a refining unit.

SUMMARY OF THE INVENTION

Apparatus, which measures the wax contents of waxy oil, includes a boiling point analyzer receiving waxy oil and providing a signal corresponding to a boiling point of the waxy oil. A gravity analyzer receiving the waxy oil and providing a signal corresponding to the gravity of the waxy oil. A viscosity analyzer receiving the waxy oil and providing a signal corresponding to the viscosity of the waxy oil. A computing circuit receives signals from all the analyzers and provides a signal corresponding to the wax content of the waxy oil in accordance with the signals from the analyzers.

The objects and the advantages of the invention will appear hereafter from a consideration of the detailed description which follows, taking together with the accompanying drawings, wherein two embodiments of the invention are illustrated by way of example. It is to be especially understood, however, that the drawings are for illustration purposes only, and are not to be construed as defining the limits of the invention.

DESCRIPTION OF THE INVENTION

Figure 1:
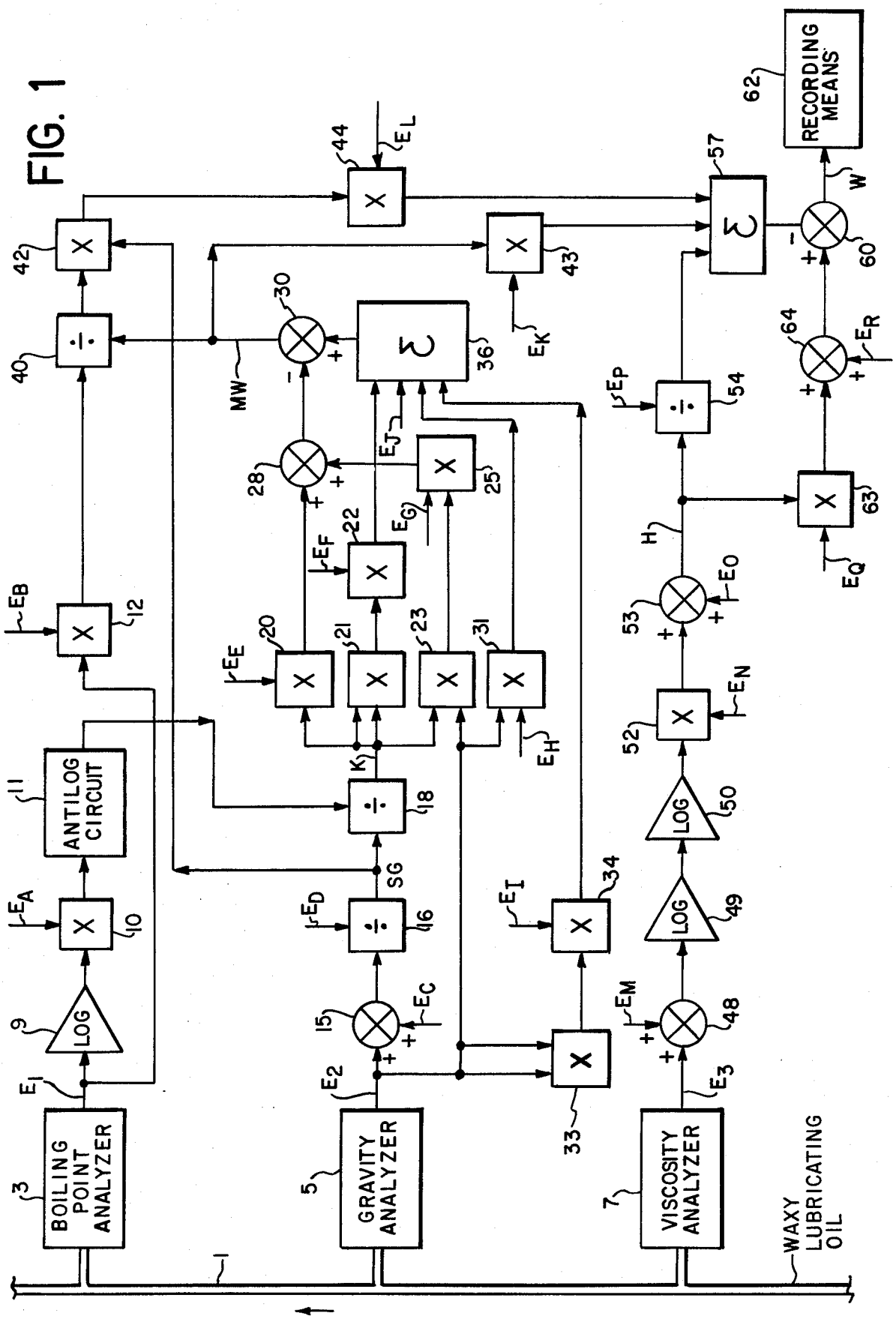
FIG. 1 is a block diagram of apparatus, constructed in accordance with the present invention for measuring the wax content of waxy oil.

The wax content W of waxy lubricating oil may be determined from the following equations.

$$W = C_1 - C_2/H + C_3 H - C_4(MW) - C_5(IP) \quad (1)$$

$$IP = (\lambda)(SG) \quad (2)$$

$$\lambda = [C_6(50\%BP)]/MW \quad (3)$$

$$SG = C_7/(A + C_8) \quad (4)$$

$$H = C_9 \log_{10} \log_{10}(V + C_{10}) + C_{11} \quad (5)$$

$$MW = C_{12} + C_{13}A - C_{14}K - C_{15}(A)(K) + C_{16}A^2 + C_{17}K^2 \quad (6)$$

$$K = \sqrt[3]{50\%BP/SG} \quad (7)$$

An alternative equation for determining the wax content is $$W = C_{18} - C_{19}(SG) + C_{20} H C_{21}(MW) \quad (8)$$

In the foregoing equations $C_1$ through $C_{21}$ are constants; having preferred values of 168.60, 41.8319, 0.08643, 0.16286, 2.6377, 0.5555, 141.5, 131.5, 870, 0.6, 154, 7955.152, 107.0542, 1768.43, 12.14112, 0.3711237, 100.1778, 257.50, 239.206, 0.078178 and 0.10354; $W$ is the wax content of the waxy oil by percent weight, $H$ is the Bell and Sharp viscosity blending value for the temperature at which the viscosity is measured, $MW$ is the average molecular weight of the waxy oil, $IP$ is the internal pressure of the waxy oil, $\lambda$ is the latent heat of vaporization of the waxy oil, $SG$ is the specific gravity of the waxy oil, $A$ is the API gravity, $V$ is the kinematic viscosity and $K$ is the Watson Characterization factor, and 50% BP is the 50 percent boiling point in degrees Rankin.

Referring to FIG. 1, waxy oil flows through a line 1. Conventional type boiling point analyzer 3, gravity analyzer 5 and viscosity analyzer 7, samples the waxy oil and provides signals $E_1$, $E_2$ and $E_3$, respectively, corresponding to the 50 percent boiling point, to the API gravity and to the kinematic viscosity, respectively, of the waxy oil. A logarithmic amplifier 9 provides a signal corresponding to the logarithm of signal $E_1$. A multiplier 10 multiplies the signal from amplifier 9 with a direct current voltage $E_A$, corresponding to a vaalue of ⅓, to provide a signal corresponding to ⅓ log 50% BP. A source of direct current voltages provides voltage $E_A$ along with voltages $E_B$ through $E_R$. The voltage source is not shown for convenience.

The signal from multiplier 10 is provided to an antilog circuit 11 which provide a signal corresponding to the cube root of the 50 percent boiling point. A multiplier 12 multiplies the signal $E_1$ with voltage $E_B$, corresponding to the constant $C_6$, to provide a signal corresponding to the numerator of equation 3.

Summing means 15 sums signal $E_2$ with voltage $E_C$ corresponding to the constant $C_8$. A divider 16 divides voltage $E_D$, corresponding to the constant $C_7$, with the signal provided by summing means 15 to provide a signal SG corresponding to the specific gravity of the waxy oil in line 1. A divider 18 divides the signal from circuit 11 with signal SG to provide a signal K corresponding to the Watson characterization factor.

Signal K is multiplied with voltage $E_E$ by a multiplier 20 to provide a signal corresponding to $C_{14}$ K.

The K signal is effectively squared by multiplier 21 which provides a corresponding signal to another multiplier 22. Multiplier 22 multiplies the signal from multiplier 21 with voltage $E_F$. Multiplier 22 provides a signal corresponding to the term $C_{17} K^2$ in equation 6. A multiplier 23 multiplies the K signal with signal $E_2$ to provide a signal corresponding to the term [A] [K]. Another multiplier 25 multiplies the signal provided by multiplier 23 with voltage $E_G$. Multiplier 25 provides a signal corresponding to the term $C_{15}$ [A] [K]. Summing means 28 sums the signals from multipliers 20, 25 to provide a signal to subtracting means 30.

A multiplier 31 multiplies signal $E_2$ with voltage $E_H$ to provide a signal corresponding to $C_{13}A$ in equation 6. Signal $E_2$ is effectively squared by multiplier 33 to provide a signal to another multiplier 34. Multiplier 34 multiplies the signal from multiplier 33 with voltage $E_I$ to provide a signal corresponding to the term $C_{16}A^2$. Summing means 36 sums the signals from multipliers 22, 31 and 34 with voltage $E_J$ to provide a sum signal to subtracting means 30. Subtracting means 30 subtracts the signal provided by summing means 28 from the signal provided by summing means 36 to provide a signal MW corresponding to the average molecular weight of the waxy oil in line 1.

A divider 40 divides the signal from multiplier 12 with the MW signal to provide a signal $\lambda$ corresponding to the latent heat of vaporization. A multiplier 42 multiplies the $\lambda$ signal with the SG signal to provide a signal IP corresponding to the internal pressure of the waxy oil.

The MW signal from summing means 30 is multiplied with voltage $E_K$ by a multiplier 43 to provide a signal corresponding to the term $C_4[MW]$ in equation 1. A multiplier 44 multiplies the IP signal with voltage $E_L$ to provide a signal corresponding to the term $C_5[IP]$.

Summing means 48 sums signal $E_3$ with voltage $E_M$ to provide a signal corresponding to the term $[V+C_{10}]$. The signal from summing means 48 is applied to a logarithmic amplifier 49 whose output in turn is applied to another logarithmic amplifier 50. Amplifier 50 provides a signal corresponding to the term $\log_{10} \log_{10} [V+C_{10}]$. A multiplier 52 multiplies the signal from amplifier 50 with voltage $E_N$, corresponding to the term $C_9$ in equation (5). Summing means 52 sums the signal from multiplier 52 with the voltage $E_0$ corresponding to the term $C_{11}$ of equation (5) to provide a signal H corresponding to the term H in equation (5).

A divider 54 divides voltage $E_P$ corresponding to the constant $C_2$, with the H signal to provide a signal corresponding to $C_2/H$. Summing means 57 sums the signal form multipliers 43 and 44 with the signal from divider 54 to provide an input to subtracting means 60.

A multiplier 63 multiplies the H signal with voltage $E_Q$ to provide a signal corresponding to term $C_3H$. Summing means 64 sums the signal from multiplier 63 with voltage $E_R$, corresponding to constant $C_1$ in equation (1), to provide a signal to subtracting means 60. Subtracting means 60 subtracts the signal provided by summing means 57 from the signal provided by summing means 64 to provide a signal W corresponding to the wax content of the oil in line 1 to recording means 62.

Figure 2:
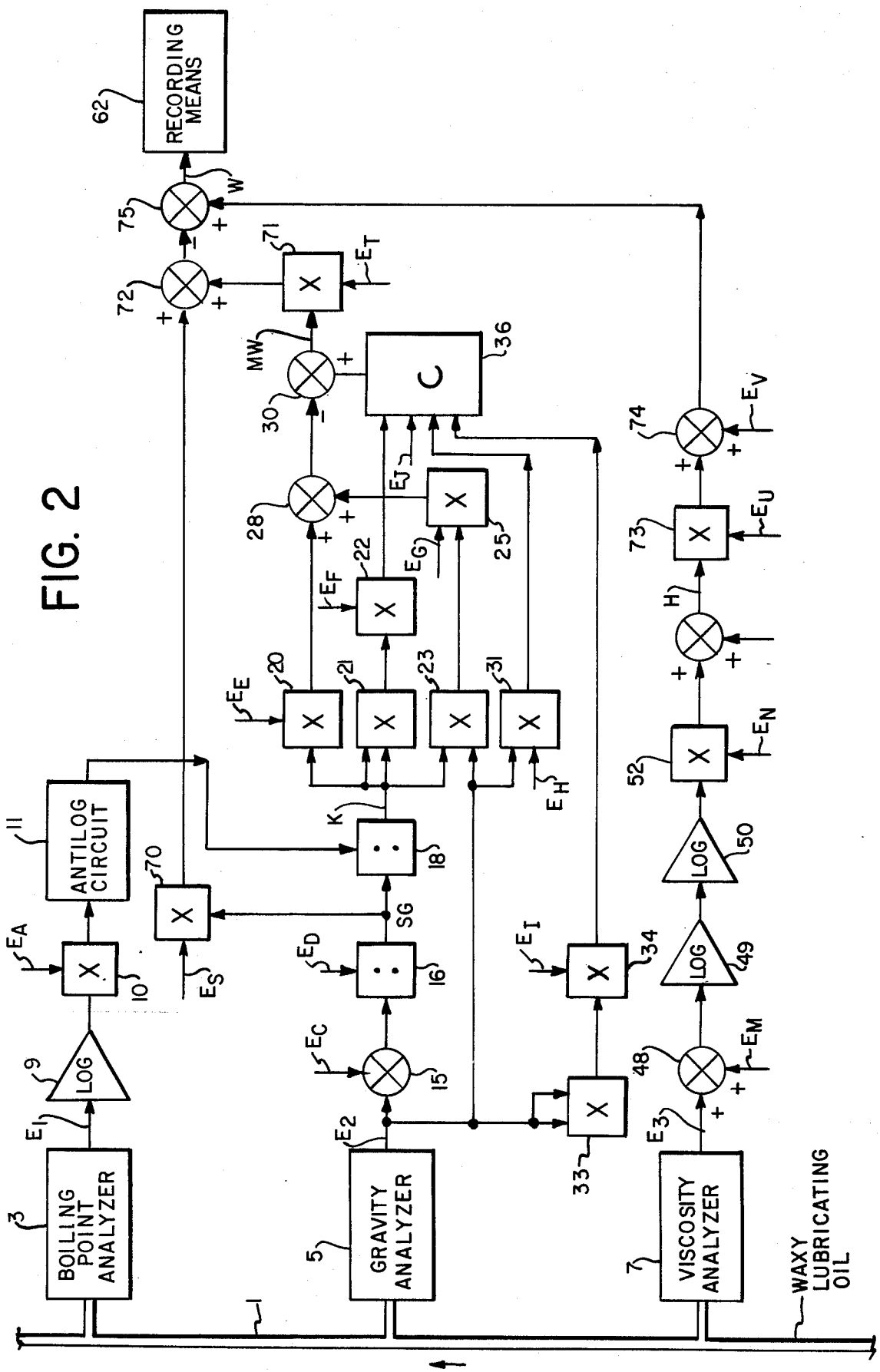
FIG. 2 is a block diagram of another embodiment of apparatus, constructed in accordance with the present invention, for measuring the waxy content of waxy oil.

Referring to FIG. 2, there is shown another embodiment of the present invention which uses equation 8. Those elements having the same elements as numbers shown in FIG. 1 perform the same functions. Thus, boiling point analyzer 3, gravity analyzer 5 and viscosity analyzer 7 provide signals $E_1$, $E_2$ and $E_3$, respectively, corresponding to the 50 percent boiling point, the API gravity, the kinematic viscosity, respectively, of the waxy oil flowing through line 1. Elements 9, 10 and 11 cooperate with analyzer 3, as hereinbefore explained, to provide a signal corresponding to the numerator in equation 7. Elements 15, 16 and 18 cooperate with analyzer 5 and circuit 11 to provide the K signal as hereinbefore explained. In addition to elements 9 through 18, multipliers 20, 21, 22, 23, 25, 31, 33 and 34, summing means 28 and 36 and subtracting means to cooperate as hereinbefore explained to provide the signal MW corresponding to the average molecular weight of the waxy oil in line 1.

Similarly, summing means 48 and 53, logarithmic amplifies 49 and 50, and multiplier 52 cooperate to provide the H signal as hereinbefore explained.

A multiplier 70 multiplies the SG signal with voltage $E_S$ to provide a signal corresponding to the term $C_{19}[SG]$. A multiplier 71 multiplies the MW signal with voltage $E_T$ to provide a signal corresponding to the term $C_{21}[NW]$. Summing means 72 sums the signals from multipliers 70, 71.

A multiplier 73 multiplies the H signal with voltage $E_U$ to provide a signal corresponding to the term $C_{20}H$. Summing means 74 sums the signal from multiplier 73 with voltage $E_V$ corresponding to the term $C_{18}$. Subtracting means 75 subtract the signal provided by summing means 72 from the signal provided by summing means 74 to provide signal W, corresponding to the wax content of the waxy oil in line 1, to recorder means 62.

The apparatus of the present invention hereinbefore described measures and records the wax content of waxy oil. The 50% boiling point, the API gravity and the kinematic viscosity of the waxy oil are sensed. The wax content is determined from the sensed parameters.

What is claimed is:

1. Means for measuring the wax content of waxy oil, comprising means for sensing a boiling point of the waxy oil and providing a corresponding signal, means for sensing the gravity of the waxy oil and providing a signal corresponding thereto, means for sensing the viscosity of the waxy oil and providing a signal representative thereof, and means connected to all the sensing means for providing a signal corresponding to the wax content of the waxy oil in accordance with the signals from the sensing means.

2. Measuring means as described in claim 1 in which the sensed boiling point is the 50% boiling point, the sensed gravity is the API gravity and the sensed viscosity is the kinematic viscosity.

3. Measuring means as described in claim 2 in which the wax content signal means includes means connected to the boiling point sensing means for providing a signal corresponding to the cube root of the 50% boiling point of the waxy oil in accordance with the boiling point signal, means connected to the gravity sensing means for providing an SG signal corresponding to the specific gravity of the waxy oil in accordance with the API gravity signal from the gravity sensing means, means connected to the specific gravity signal wax content network means and to the cube root signal means for providing a K signal corresponding to the Watson characterization factor K, in accordance with the cube root signal and the SG signal, means connected to the K signal means and to the gravity sensing means for providing an MW signal corresponding to the average molecular weight of the waxy oil in accordance with the API gravity signal and the K signal, means connected to the viscosity sensing means for providing a signal corresponding to the viscosity blending value H in accordance with kinematic viscosity signal from the viscosity sensing means, means connected to the boiling point sensing means and to the MW signal means for providing a λ signal corresponding to latent heat of vaporization in accordance with the cube root signal and the MW signal, means connected to the λ signal means and to the specific gravity signal means for providing an IP signal corresponding to the internal pressure of the waxy oil, and means connected to the IP signal means, to the MW signal and to the H signal means for providing the signal corresponding to the wax content of the waxy oil.

4. Measuring means as described in claim 3 in which the K signal means provides the K signal in accordance with the following equation:

$$K = \sqrt[3]{50\% PB}/SG$$

where 50% BP is the 50% boiling point of the waxy oil.

5. Measuring means as described in claim 4 in which the SG signal means provides the SG signal in accordance with the following equation:

$$SG = C_7/(A+C_8)$$

where $C_7$ and $C_8$ are constants, and $A$ is the API gravity of the waxy oil.

6. Measuring means as described in claim 5 in which the MW signal means provides the MW signal in accordance with the following equation:

$$MW = C_{12} + C_{13}A - C_{14}K - C_{15}(A)(K) + C_{16}A^2 + C_{17}K$$

where $C_{12}$, $C_{13}$, $C_{14}$, $C_{15}$, $C_{16}$ and $C_{17}$ are constants.

7. Measuring means are described in claim 6 in which the H signal means provides the H signal in accordance with the following equation:

$$H = C_9 \log_{10}\log_{10}(V + C_{10}) + C_{11}$$

where $C_9$, $C_{10}$ and $C_{11}$ are constants and $V$ is the kinematic viscosity of the waxy oil.

8. Measuring means as described in claim 7 in which the λ signal means provides the λ signal in accordance with the following equation:

$$\lambda = C_6 (50\% BP)/MW$$

where $C_6$ is a constant.

9. Measuring means as described in claim 8 in which the IP signal means provides the IP signal in accordance with the following equation:

$$IP = (\lambda)(SG)$$

10. Measuring means as described in claim 9 in which the wax content network means provides the wax content signal in accordance with the following equation:

$$W = C_1 - C_2/H + C_3 H - C_4(MW) - C_5 (IP)$$

where $C_1$, $C_2$, $C_3$, $C_4$ and $C_5$ are constants and $W$ corresponds to the wax content of the waxy oil.

11. Measuring means as described in claim 10 in which the temperature of the waxy oil in the viscosity sensing means is substantially 210°F and the constants $C_1$ through $C_{17}$ have preferred values of: 168.60, 41.8319, 0.08643, 0.16286, 2.6377, 0.5555, 141.5, 131.5, 870, 0.6, 154, 7955.152, 107.0542, 1768.43, 12.14112, 0.3711237, and 100.1778, respectively.

12. Measuring means as described in claim 2 in which the wax content signal means includes means connected to the boiling point sensing means for providing a signal corresponding to the cube root of the 50% boiling point of the waxy oil in accordance with the boiling point signal, means connected to the gravity sensing means for providing an SG signal corresponding to the specific gravity of the waxy oil in accordance with signal from the gravity sensing means, means connected to the cube root signal means in specific gravity signal means for providing a K signal corresponding to the Watson characterization factor K, means connected to the K signal means and to the gravity sensing means for providing an MW signal corresponding to the average molecular weight of the waxy oil, and means connected to viscosity sensing means for providing a signal corresponding to the viscosity blending value H of the waxy oil, circuit means connected to the SG signal means, to the MW signal means and to the H signal means for providing the signal corresponding to the wax content of the waxy oil.

13. Measuring means as described in claim 12 in which the K signal means provides the K signal in accordance with the following equation:

$$K = \sqrt[3]{50\% BP}/SG$$

where 50% BP is the 50 percent boiling point of the waxy oil.

14. Measuring means as described in claim 13 in which the SG signal means provides a specific gravity signal in accordance with the following equation:

$$SG = C_7/(A + C_8)$$

where $C_7$ and $C_8$ are constants and $A$ is the API gravity of the waxy oil.

15. Measuring means as described in claim 14 in which the MW signal means provides the MW signal in accordance with the following equation:

$$MW = C_{12} + C_{13}A - CK - C_{15}(A)(K) + C_{16}A^2 + C_{17}K^2$$

where $C_{12}$ through $C_{17}$ are constants.

16. Measuring means as described in claim 15 in which the H signal means provides the H signal in accordance with the following equation:

$$H = C_9 \log_{10} \log_{10}(V + C_{10}) + C_{11}$$

where $C_9$, $C_{10}$ and $C_{11}$ are constants and V is the kinematic viscosity of the waxy oil.

17. Measuring means as described in claim 16 in which the wax content signal circuit means provides the wax content signal in accordance with the following equation:

$$W = C_{18} - C_{19}(SG) + C_{20}H - C_{21}(MW)$$

where $C_{18}$, $C_{19}$, $C_{20}$ and $C_{21}$ are constants and $W$ is the wax content of the waxy oil.

18. Measuring means as described in claim 17 in which the temperature of the waxy oil in the viscosity sensing means is substantially 210°F and constants $C_7$ through $C_{21}$ have preferred values of 141.5, 131.5, 870, 0.6, 154, 7955.152, 107.0542, 1768.43, 12.14112, 0.3711237, 100.1778, 257.50, 239,206, 0.078178 and 0.10354, respectively.

* * * * *

UNITED STATES PATENT AND TRADEMARK OFFICE
CERTIFICATE OF CORRECTION

PATENT NO. : 3982422
DATED : September 28, 1976
INVENTOR(S) : C.W.Harrison, T.C.Mead, H.R.Moreland, F.L.Barger It is certified that error appears in the above–identified patent and that said Letters Patent are hereby corrected as shown below:

Col. 4, Claim 3, line 34:

"wax content network means" should read --means--.

Col. 4, Claim 3, line 53:

"and means" should read --and wax content network means--

Signed and Sealed this

Thirty-first Day of May 1977

[SEAL]

Attest:

RUTH C. MASON
Attesting Officer

C. MARSHALL DANN
Commissioner of Patents and Trademarks